United States Patent
Iwabuchi et al.

(10) Patent No.: US 9,428,488 B2
(45) Date of Patent: Aug. 30, 2016

(54) METHOD FOR PRODUCING 4-[5-(PYRIDIN-4-YL)-1H-1,2,4-TRIAZOL-3-YL]PYRIDINE-2-CARBONITRILE, AND INTERMEDIATE THEREOF

(71) Applicant: FUJIYAKUHIN CO., LTD., Saitama-shi (JP)

(72) Inventors: Yoshiyuki Iwabuchi, Saitama (JP); Sachiho Miyata, Saitama (JP); Junichiro Uda, Saitama (JP); Osamu Nagata, Saitama (JP)

(73) Assignee: FUJIYAKUHIN CO., LTD., Saitama-shi (JP)

( * ) Notice: Subject to any disclaimer, the term of this patent is extended or adjusted under 35 U.S.C. 154(b) by 0 days.

(21) Appl. No.: 14/406,637

(22) PCT Filed: Jul. 24, 2013

(86) PCT No.: PCT/JP2013/070005
§ 371 (c)(1),
(2) Date: Dec. 9, 2014

(87) PCT Pub. No.: WO2014/017516
PCT Pub. Date: Jan. 30, 2014

(65) Prior Publication Data
US 2015/0166510 A1 Jun. 18, 2015

(30) Foreign Application Priority Data
Jul. 25, 2012 (JP) .................................. 2012-177538

(51) Int. Cl.
C07D 401/14 (2006.01)
C07D 213/86 (2006.01)
C07D 213/84 (2006.01)
C07D 213/89 (2006.01)

(52) U.S. Cl.
CPC ........... *C07D 401/14* (2013.01); *C07D 213/84* (2013.01); *C07D 213/86* (2013.01); *C07D 213/89* (2013.01)

(58) Field of Classification Search
CPC .................................................. C07D 401/14
USPC ........................................................ 546/256
See application file for complete search history.

(56) References Cited

U.S. PATENT DOCUMENTS

| 4,788,210 A | 11/1988 | Luethy et al. |
| 2005/0004175 A1 | 1/2005 | Nakamura et al. |
| 2006/0189811 A1 | 8/2006 | Nakamura et al. |

FOREIGN PATENT DOCUMENTS

| JP | 61-152661 A | 7/1986 |
| JP | 2005-041802 A | 2/2005 |
| WO | 03/064410 A1 | 8/2003 |
| WO | 2005/009991 A1 | 2/2005 |

OTHER PUBLICATIONS

International Search Report and Written Opinion issued Oct. 22, 2013 in PCT/JP2013/070005 filed Jul. 24, 2013.
Takahiro Sato, et al., "Discovery of 3-(3-cyano-4-pyridyl)-5-(4-pyridyl)-1,2,4-triazole, FYX-051—a xanthine oxidoreductase inhibitor for the treatment of hyperuricemia" Bioorganic & Medicinal Chemistry Letters, vol. 19, No. 21, 2009, pp. 6225-6229.

(Continued)

*Primary Examiner* — Patricia L Morris
(74) *Attorney, Agent, or Firm* — Oblon, McClelland, Maier & Neustadt, L.L.P.

(57) ABSTRACT

To provide an industrially useful method for producing pharmaceutically useful 4-[5-(pyridin-4-yl)-1H-1,2,4-triazol-3-yl]pyridine-2-carbonitrile, and an intermediate for producing the compound.

The method for producing compound represented by formula (1) is represented by the following reaction scheme, and the intermediate is represented by the following formula (4).

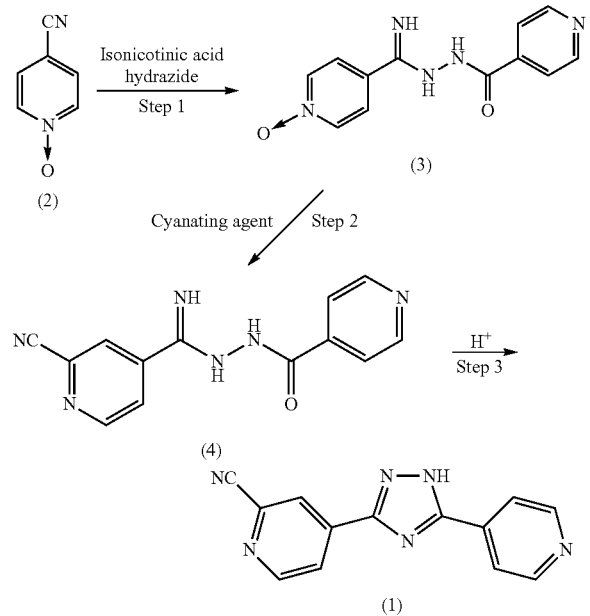

17 Claims, No Drawings

(56) References Cited

OTHER PUBLICATIONS

Zhibao Huo, et al., "Zinc cyanide mediated direct α-cyanation of isonicotinic acid N-oxide. Application to the synthesis of FYX-051, a xanthine oxidoreductase inhibitor" Tetrahedron Letters, vol. 49, No. 28, 2008, pp. 4369-4371.

A.V. Sergievskii, et al., "Reactions of Methyl 4-Aminofurazan-3-carboximidate with Nitrogen-Containing Nucleophiles*" Russian Journal of Organic Chemistry, vol. 37, No. 5, 2001, pp. 717-720.

METHOD FOR PRODUCING 4-[5-(PYRIDIN-4-YL)-1H-1,2,4-TRIAZOL-3-YL]PYRIDINE-2-CARBONITRILE, AND INTERMEDIATE THEREOF

TECHNICAL FIELD

The present invention relates to a method for producing 4-[5-(pyridin-4-yl)-1H-1,2,4-triazol-3-yl]pyridine-2-carbonitrile, serving as a useful pharmaceutical, and to a novel intermediate useful for producing the compound.

BACKGROUND ART

Compound (1), 4-[5-(pyridin-4-yl)-1H-1,2,4-triazol-3-yl]pyridine-2-carbonitrile, is known to serve as a drug which has a xanthine oxidase inhibitory action and which can lower serum uric acid level (Patent Document 1).

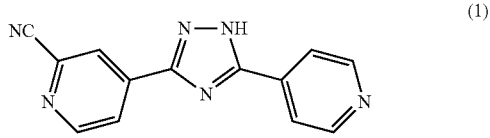 [SMILES: N#Cc1cc(-c2n[nH]c(-c3ccncc3)n2)ccn1]

(1)

There have been reported several methods for producing the above compound (1). In one production method, methyl isonicotinate N-oxide is subjected to Reissert Henze reaction, to thereby form methyl 2-cyanoisonicotinate, which is transformed into a hydrazide, and the hydrazide is condensed with 4-cyanopyridine (Patent Document 1, Example 12). In another production method, isonicotinic acid N-oxide is transformed into a hydrazide, into which a cyano group is incorporated through Reissert Henze reaction, and the product is condensed with 4-cyanopyridine (Patent Document 1, Example 39). In an alternative production method, 4-cyanopyridine-N-oxide (starting material) is condensed with isonicotinic acid hydrazide, to thereby form a triazole ring, which is then protected (Patent Document 2) or non-protected (Patent Document 3), and a cyano group is incorporated into the product through Reissert Henze reaction, to thereby yield compound (1).

CITATION LIST

Patent Document

Patent Document 1: WO2003/064410
Patent Document 2: WO2005/009991
Patent Document 3: JP-A-2005-41802

SUMMARY OF THE INVENTION

Problems to be Solved by the Invention

However, the method disclosed in Patent Document 1, which can satisfactorily attain the production purpose only on a small scale, has problems. For example, production of substituted or unsubstituted 2-cyanoisonicotinic acid hydrazide is cumbersome, and requires use of a reaction solvent suitable for physical properties of a product compound in each step. An isolation operation must be performed in each step. In addition, the total yield of this method is not satisfactory, thereby making the method not suited for industrial production. The method disclosed in Patent Document 2 involves a number of reaction steps due to protection of a triazole ring, whereby the method is not advantageous for industrial operation from the viewpoint of production cost. The method disclosed in Patent Document 3 is not suited for industrial production, since the method requires a plurality of purification steps for decoloration and for removal of impurities.

Thus, an object of the present invention is to provide an industrially useful method for producing pharmaceutically useful 4-[5-(pyridin-4-yl)-1H-1,2,4-triazol-3-yl]pyridine-2-carbonitrile.

Means for Solving the Problems

The present inventors have conducted extensive studies on the method for producing 4-[5-(pyridin-4-yl)-1H-1,2,4-triazol-3-yl]pyridine-2-carbonitrile, and have found that the target compound can be produced via a novel intermediate, 4-pyridinecarboxylic acid N'-(2-cyanopyridine-4-carbonimidoyl)hydrazide, to thereby provide an industrially useful production method therefor. The present invention has been accomplished on the basis of this finding.

Accordingly, the present invention provides the following [1] to [4].

[1] 4-Pyridinecarboxylic acid N'-(2-cyanopyridine-4-carbonimidoyl)hydrazide represented by the following formula (4):

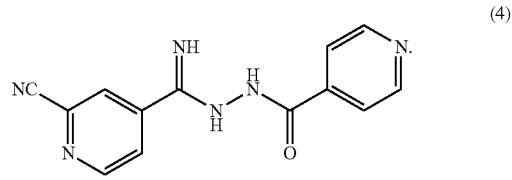 [SMILES: N#Cc1cc(C(=N)NNC(=O)c2ccncc2)ccn1]

(4)

[2] A method for producing a compound as recited in [1] above, the method comprising reacting a compound represented by the following formula (2):

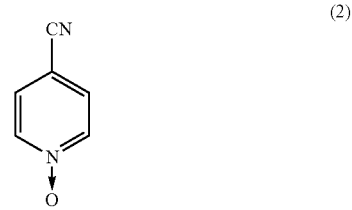

(2)

with isonicotinic acid hydrazide in the presence of an alkali metal alkoxide, to thereby form a compound represented by the following formula (3):

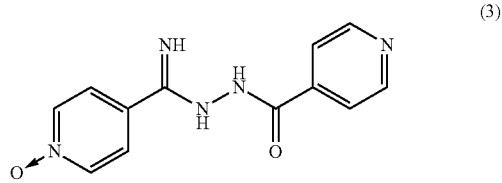 [SMILES: N=C(NNC(=O)c1ccncc1)c1cc[n+]([O-])cc1]

(3)

and cyanating the compound (3) with a cyanating agent.

[3] A method for producing 4-[5-(pyridin-4-yl)-1H-1,2,4-triazol-3-yl]pyridine-2-carbonitrile, represented by the following formula (1):

the method comprising reacting a compound represented by the following formula (2):

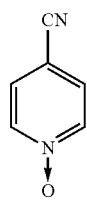
(2)

with isonicotinic acid hydrazide in the presence of an alkali metal alkoxide, to thereby form a compound represented by the following formula (3):

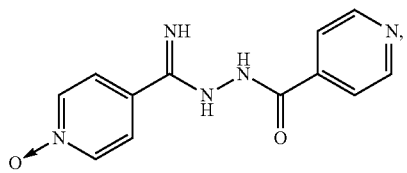
(3)

cyanating the compound (3) with a cyanating agent, to thereby form a compound represented by the following formula (4):

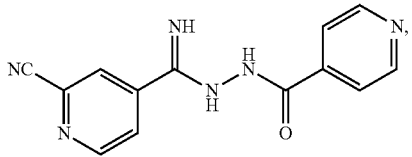
(4)

and subjecting the compound (4) to a ring-closure reaction in the presence of an acid catalyst.

[4] A method for producing 4-[5-(pyridin-4-yl)-1H-1,2,4-triazol-3-yl]pyridine-2-carbonitrile, represented by the following formula (1):

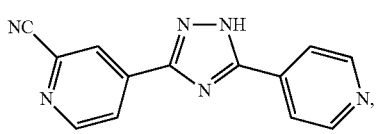
(1)

the method comprising subjecting a compound represented by the following formula (4):

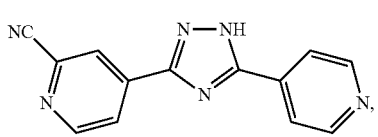
(4)

to a ring-closure reaction in the presence of an acid catalyst.

Effects of the Invention

According to the production method of the present invention, there can be produced 4-[5-(pyridin-4-yl)-1H-1,2,4-triazol-3-yl]pyridine-2-carbonitrile, which serves as a useful drug having a xanthine oxidase inhibitory action, in simple steps at high yield with a reduced amount of by-products.

MODES FOR CARRYING OUT THE INVENTION

The present invention will next be described in detail.
The method of the present invention is represented by the following reaction scheme.

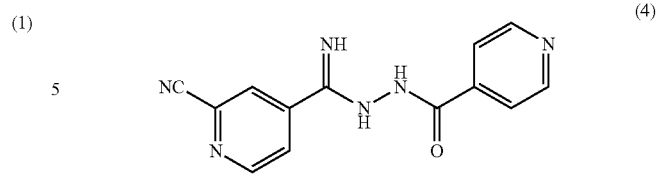

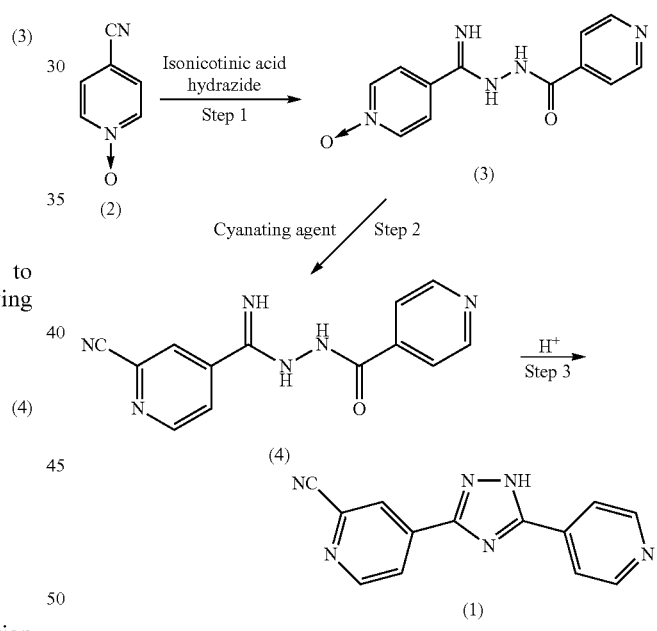

(Step 1)

In step 1, 4-cyanopyridine-N-oxide (2) is reacted with isonicotinic acid hydrazide in the presence of an alkali metal alkoxide, to thereby form compound (3).

The reactants, 4-cyanopyridin-N-oxide (2) and isonicotinic acid hydrazide, are known compounds which may be produced through means known per se.

The alkali metal alkoxide employed in the reaction is preferably an alkali metal C1-C6 alkoxide. Specific examples thereof include sodium methylate and sodium ethylate. The reaction is preferably performed in a solvent, and the solvent is preferably an alcoholic solvent such as methanol or ethanol.

In a preferred mode of the above reaction, compound (2) is treated with an alkali metal alkoxide in a solvent, and then reacted with isonicotinic acid hydrazide. The reaction between compound (2) and the alkali metal alkoxide is performed under cooling to reflux conditions, preferably at 15° C. to 80° C. The reaction time is generally about 30 minutes to about 12 hours, preferably about 1 to about 4 hours. The subsequent reaction with isonicotinic acid hydrazide is performed under the same temperature conditions in an equivalent amount or an excess (or deficient) amount. The reaction time is generally about 30 minutes to about 12 hours, preferably about 1 to about 5 hours.
(Step 2)

In step 2, compound (3) is cyanated with a cyanating agent, to thereby form compound (4).

Examples of the cyanating agent employed in the reaction include alkali metal cyanides such as sodium cyanide and potassium cyanide; zinc cyanide; and trialkyl cyanides such as trimethylsilyl cyanide.

Preferably, the cyanation is performed in accordance with, for example, Reissert Henze reaction (Heterocycles, Vol. 22, No. 5, 1994). In one mode of the cyanation, compound (3) is activated with an alkylcarbamoyl halide in an organic solvent, and then the activated species is reacted with a cyanating agent, to thereby form compound (4). The alkylcarbamoyl halide which may be used in carbamoylation, the first step of Reissert Henze reaction, is preferably a di(C1-C6 alkyl)carbamoyl halide such as dimethylcarbamoyl chloride or dipropylcarbamoyl chloride. Of these, dimethylcarbamoyl chloride is preferred. Examples of the solvent which may be used in the reaction include N,N-dimethylformamide, N,N-dimethylacetamide, N-methylpyrrolidone, tetrahydrofuran, and acetonitrile. Of these, N,N-dimethylformamide is preferred. The reaction temperature is preferably 15 to 60° C., more preferably 30 to 50° C. The reaction time is preferably 1 to 24 hours, more preferably 1 to 3 hours. The cyanating agent which may be employed in the subsequent cyanation is the same as exemplified above. Sodium cyanide, potassium cyanide, zinc cyanide, trimethylcyanide, and the like are preferred, with sodium cyanide being more preferred. The reaction temperature is preferably −20 to 60° C., more preferably −10 to 40° C. Cyanation is performed with stirring for 1 to 4 hours.

Compound (4) yielded in step 2 is a novel compound and serves as a useful intermediate for producing compound (1). Compound (4) can be readily synthesized at high yield in step 2, without performing purification. Compound (1) can be efficiently produced via compound (4) on an industrial scale.
(Step 3)

In step 3, compound (4) is subjected to a ring-closure reaction in the presence of an acid catalyst, to thereby form compound (1).

Organic acids and inorganic acids such as phosphoric acid, p-toluenesulfonic acid, and hydrochloric acid may be employed in the reaction. Among them, an inorganic acid is preferred, with phosphoric acid being particularly preferred. As a reaction solvent, water, an alcohol such as 2-butanol, 2-propanol, or ethanol, or a mixed solvent of water and an alcohol may be used. Among them, a mixed solvent of water and 2-butanol at a ratio of 5:1 to 10:1 is preferred. The reaction temperature is 60 to 100° C., preferably 70 to 90° C., and the reaction time is 2 to 12 hours, preferably 8 to 10 hours. The reaction is preferably performed under stirring.

The intermediate and compound (1) in the method of the present invention may be isolated from a reaction mixture and purified through a routine technique such as washing, recrystallization, and chromatographic techniques.

EXAMPLES

The present invention will next be described in detail by way of Examples, which should not be construed as limiting the invention thereto.

In the Examples, used are the following abbreviations: $^1$H-NMR: proton nuclear magnetic resonance spectrum, DMSO-$d_6$: deuterated dimethylsulfoxide, Hz: hertz, J: coupling constant, s: singlet, dd: double doublet, d: doublet, and br: broad. The "NMR" refers to a 270 MHz nuclear magnetic resonance spectrum measured by use of TMS (tetramethylsilane) as an internal standard. The "MS" refers to mass spectrometry by means of a mass spectrometer employing ESI (electro-spray ionization method).

Example 1

Synthesis of N"-(4-pyridinecarbonyl)-4-pyridinehydrazideimide-1-oxide (3)

4-Cyanopyridine-N-oxide (2) (5.00 g) was suspended in methanol (40 mL), and sodium methylate (22.4 mg) was added to the suspension. The mixture was stirred under nitrogen at 40° C. for 2 hours. Isonicotinic acid hydrazide (5.71 g) was added to the mixture at 40° C., and the resultant mixture was stirred at 40° C. for 4 hours. The reaction mixture was cooled to room temperature, and precipitated crystals were recovered through filtration. The crystals were washed with methanol (15 mL) and then dried at 80° C. for 15 hours, to thereby yield 9.60 g of N"-(4-pyridinecarbonyl)-4-pyridinehydrazideimide-1-oxide (3).

$^1$H-NMR (DMSO-$d_6$) δ (ppm): 6.98 (br, 2H), 7.81 (d, 2H, J=5.77 Hz), 7.85 (d, 2H, J=7.09 Hz), 8.29 (d, 2H, J=7.09 Hz), 8.73 (d, 2H, J=5.77 Hz), 10.37 (br, 1H)

MS m/z: 256 [M-H]$^-$

Example 2

Synthesis of 4-pyridinecarboxylic acid N'-(2-cyanopyridine-4-carbonimidoyl)hydrazide (4)

N"-(4-Pyridinecarbonyl)-4-pyridinehydrazideimide-1-oxide (3) (10.0 g) was suspended in N,N-dimethylformamide (48 mL), and dimethylcarbamoyl chloride (9.20 g) was added to the suspension under nitrogen at 40° C., followed by stirring for 1 hour. Sodium cyanide (2.48 g) was added to the resultant mixture at 40° C., and stirring was further performed for 1 hour. The reaction mixture was cooled to ≤5° C., and 5% aqueous sodium hydrogen carbonate solution (100 mL) and water (100 mL) were sequentially added dropwise thereto. Precipitated crystals were recovered through filtration. The crystals were washed with water (100 mL) and then dried at 80° C. for 15 hours under reduced pressure, to thereby yield 9.28 g of 4-pyridinecarboxylic acid N'-(2-cyanopyridine-4-carbonimidoyl)hydrazide (4).

$^1$H-NMR (DMSO-$d_6$) δ (ppm): 7.15 (br, 2H), 7.82 (d, 2H, J=5.61 Hz), 8.14 (d, 1H, J=5.11 Hz), 8.37 (s, 1H), 8.75 (d, 2H, J=5.61 Hz), 8.86 (d, 1H, J=5.11 Hz), 10.47 (br, 1H)

MS m/z: 265 [M-H]$^-$

Example 3

Synthesis of 4-[5-(pyridin-4-yl)-1H-1,2,4-triazol-3-yl]pyridine-2-carbonitrile (1)

Water (82 mL), 2-butanol (8.2 mL), and phosphoric acid (4.00 g) were added to 4-pyridinecarboxylic acid N'-(2- cyanopyridine-4-carbonimidoyl)hydrazide (4) (9.25 g), and the mixture was stirred at 80° C. for 8 hours. The reaction mixture was cooled to room temperature, and precipitated crystals were recovered through filtration. The crystals were washed with a water-2-butanol (10:1) mixture (92.5 mL). The thus-washed crystal were dried at 80° C. for 13 hours under reduced pressure, to thereby yield 7.89 g of 4-[5-(pyridin-4-yl)-1H-1,2,4-triazol-3-yl]pyridine-2-carbonitrile (1).

$^1$H-NMR (DMSO-$d_6$) δ (ppm): 8.02 (dd, 2H, J=4.59, 1.62 Hz), 8.32 (dd, 1H, J=5.13, 1.62 Hz), 8.55 (dd, 1H, J=1.62, 1.08 Hz), 8.80 (dd, 2H, J=4.59, 1.62 Hz), 8.93 (dd, 1H, 5.13, 1.08 Hz)

MS m/z: 247 [M-H]$^-$

The invention claimed is:

1. A method for producing 4-[5-(pyridin-4-yl)-1H-1,2,4-triazol-3-yl]pyridine-2-carbonitrile of formula (1):

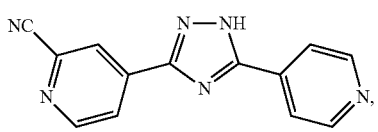

the method comprising reacting a compound of formula (2):

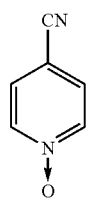

with isonicotinic acid hydrazide in the presence of an alkali metal alkoxide, to thereby form a compound of formula (3):

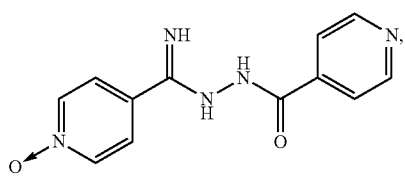

cyanating the compound (3) with at least one cyanating agent selected from the group consisting of an alkali metal cyanide, zinc cyanide, and a trialkyl cyanide, to thereby form a compound of formula (4):

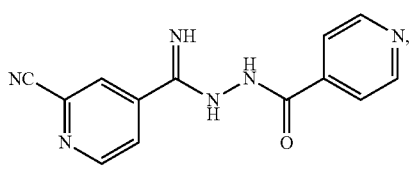

and subjecting the compound (4) to a ring-closure reaction in the presence of at least one acid catalyst selected from the group consisting of an organic acid catalyst and an inorganic acid catalyst.

2. The method of claim 1, wherein the cyanating agent is an akali metal cyanide and said alkali metal cyanide is selected from the group consisting of sodium cyanide and potassium cyanide.

3. The method of claim 1, wherein the cyanating agent is a trialkyl cyanide and said trialkyl cyanide is trimethylsilyl cyanide.

4. The method of claim 1, wherein the acid catalyst is an organic acid catalyst.

5. The method of claim 1, wherein the acid catalyst is an inorganic acid catalyst.

6. The method of claim 1, wherein the inorganic acid catalyst is selected from the group consisting of phosphoric acid, p-toluenesulfonic acid, and hydrochloric acid.

7. The method of claim 1, wherein the alkali metal alkoxide is an alkali metal $C_1$-$C_6$ alkoxide.

8. The method of claim 1, wherein said reacting the compound (2) with isonicotinic acid hydrazide in the presence of an alkali metal alkoxide is in an alcoholic solvent.

9. The method of claim 1, wherein said reacting the compound (2) with isonicotinic acid hydrazide in the presence of an alkali metal alkoxide comprises treating compound (2) with an alkali metal alkoxide in a solvent, cooling to reflux at 15° C. to 80° C. for about 30 minutes to about 12 hours, reacting compound (2) with isonicotinic acid hydrazide at 15° C. to 80° C. for about 30 minutes to about 12 hours.

10. The method of claim 1, wherein said cyanating the compound (3) with at least one cyanating agent comprises activating compound (3) with an alkylcarbamoyl halide in an organic solvent, and then the activated species is reacted with a cyanating agent.

11. The method of claim 10, wherein said alkylcarbamoyl halide is a di($C_1$-$C_6$ alkyl)carbamoyl halide.

12. The method of claim 10, wherein said organic solvent is selected from the group consisting of N,N-dimethylformamide, N,N-dimethylacetamide, N-methylpyrrolidone, tetrahydrofuran, and acetonitrile.

13. The method of claim 10, wherein said activating compound (3) with an alkylcarbamoyl halide in an organic solvent is at a reaction temperature of 15 to 60° C. for 1 to 24 hours.

14. The method of claim 10, wherein the reaction of the activated species with a cynating agent is at a reaction temperature of −20 to 60° C. for 1 to 4 hours with stirring.

15. The method of claim 1, wherein said ring-closure reaction is conducted in a reaction solvent selected from the group consisting of water, an alcohol, or a mixed solvent of water and an alcohol.

16. The method of claim 1, wherein said ring-closure reaction is conducted in a mixed solvent of water and 2-butanol at a ratio of 5:1 to 10:1.

17. The method of claim 1, wherein said ring-closure reaction is at a reaction temperature of 60 to 100° C. for 2 to 12 hours with stirring.

* * * * *